United States Patent
Olayiwola et al.

(10) Patent No.: US 12,325,684 B2
(45) Date of Patent: Jun. 10, 2025

(54) LIMITING ACETIC ACID PRODUCTION IN ETHANE ODH PROCESS

(71) Applicant: NOVA CHEMICALS (INTERNATIONAL) S.A., Fribourg (CH)

(72) Inventors: Bolaji Olayiwola, Calgary (CA); Shahin Goodarznia, Calgary (CA); Vasily Simanzhenkov, Calgary (CA); Mohamed Aiffa, Calgary (CA); Kamal Serhal, Calgary (CA); Robert Ladd, Airdrie (CA); David Gent, Red Deer (CA)

(73) Assignee: NOVA Chemicals (International) S.A., Fribourg (CH)

( * ) Notice: Subject to any disclaimer, the term of this patent is extended or adjusted under 35 U.S.C. 154(b) by 371 days.

(21) Appl. No.: 18/008,312

(22) PCT Filed: May 25, 2021

(86) PCT No.: PCT/IB2021/054554
§ 371 (c)(1),
(2) Date: Dec. 5, 2022

(87) PCT Pub. No.: WO2021/250495
PCT Pub. Date: Dec. 16, 2021

(65) Prior Publication Data
US 2023/0202958 A1   Jun. 29, 2023

Related U.S. Application Data

(60) Provisional application No. 63/036,471, filed on Jun. 9, 2020.

(51) Int. Cl.
*C07C 51/16* (2006.01)
*C07C 51/15* (2006.01)
*C07C 53/08* (2006.01)

(52) U.S. Cl.
CPC .............. *C07C 51/16* (2013.01); *C07C 51/15* (2013.01); *C07C 53/08* (2013.01)

(58) Field of Classification Search
CPC ......... C07C 51/16; C07C 51/15; C07C 53/08; C07C 2523/20; C07C 2523/22;
(Continued)

(56) References Cited

U.S. PATENT DOCUMENTS 3,509,115 A   4/1970   French
3,715,389 A   2/1973   Hoch et al.
(Continued)

FOREIGN PATENT DOCUMENTS

AU   608615   4/1991
BR   PI0707520   5/2011
(Continued)

OTHER PUBLICATIONS

Japanese Office Action in Japanese Appln. No. 2022-575246, mailed on Jan. 28, 2025, 4 pages, with English Translation.
(Continued)

*Primary Examiner* — Deborah D Carr
(74) *Attorney, Agent, or Firm* — Fish & Richardson P.C.

(57) ABSTRACT

The present disclosure relates to limiting the production of acetic acid in an oxidative dehydrogenation process to convert ethane to ethylene. The process of oxidative dehydrogenation includes feeding acetic acid, along with ethane and oxygen into an oxidative dehydrogenation reactor where contact with a catalyst leads to conversion of the ethane into ethylene and acetic acid. By including acetic acid in the feed, the amount of acetic acid produced may be limited and the ratio of ethylene produced to ethane consumed may increase.

22 Claims, 3 Drawing Sheets

(58) Field of Classification Search
CPC . C07C 2523/28; C07C 2527/057; C07C 5/48; C07C 11/04; Y02P 20/52
See application file for complete search history.

(56) References Cited

U.S. PATENT DOCUMENTS

| | | | |
|---|---|---|---|
| 4,899,003 | A | 2/1990 | Manyik et al. |
| 5,162,578 | A | 11/1992 | McCain, Jr. et al. |
| 6,576,803 | B2 | 6/2003 | Cantrell et al. |
| 6,670,504 | B1 | 12/2003 | Borchert et al. |
| 6,852,877 | B1 | 2/2005 | Zeyss et al. |
| 7,078,563 | B2 | 7/2006 | Ellis et al. |
| 7,081,549 | B2 | 7/2006 | Cook et al. |
| 7,211,688 | B2 | 5/2007 | Clarke et al. |
| 7,227,049 | B2 | 6/2007 | Liu |
| 7,304,014 | B2 | 12/2007 | Cavalcanti et al. |
| 7,390,918 | B2 | 6/2008 | Clarke et al. |
| 7,411,107 | B2 | 8/2008 | Lucy |
| 7,491,843 | B2 | 2/2009 | Jobson et al. |
| 7,635,785 | B2 | 12/2009 | Bauer et al. |
| 7,772,450 | B2 | 8/2010 | Iaccino et al. |
| 8,383,854 | B2 | 2/2013 | Ryan et al. |
| 8,426,638 | B2 | 4/2013 | McSwain et al. |
| RE44,206 | E | 5/2013 | Ferguson et al. |
| 8,440,855 | B2 | 5/2013 | Voss et al. |
| 9,156,764 | B2 | 10/2015 | Han et al. |
| 9,993,798 | B2 | 6/2018 | Simanzhenkov et al. |
| 10,329,222 | B2 | 6/2019 | Bos et al. |
| 10,427,992 | B2 | 10/2019 | Mitkidis et al. |
| 10,647,656 | B2 | 5/2020 | Lange |
| 10,815,169 | B2 | 10/2020 | Schoonebeek et al. |
| 2005/0202964 | A1 | 9/2005 | Cavalcanti et al. |
| 2008/0132723 | A1 | 6/2008 | Johnston et al. |
| 2008/0221374 | A1 | 9/2008 | Crone et al. |
| 2009/0043141 | A1 | 2/2009 | Mazanec et al. |
| 2010/0222623 | A1 | 9/2010 | Ryan |
| 2013/0261348 | A1 | 10/2013 | Scates et al. |
| 2014/0114109 | A1 | 4/2014 | Sanchez Valente et al. |
| 2014/0275619 | A1 | 9/2014 | Chen et al. |
| 2018/0009662 | A1 | 1/2018 | Simanzhenkov et al. |
| 2018/0186707 | A1 | 7/2018 | Abudawoud et al. |
| 2020/0095179 | A1 | 3/2020 | Periana et al. |
| 2020/0115637 | A1 | 4/2020 | Olayiwola et al. |
| 2020/0223768 | A1 | 7/2020 | Van Rossum et al. |
| 2020/0223769 | A1 | 7/2020 | Calvo et al. |
| 2023/0202958 | A1 | 6/2023 | Olayiwola et al. |

FOREIGN PATENT DOCUMENTS

| | | |
|---|---|---|
| CA | 2341555 | 3/2000 |
| CA | 2465380 | 7/2003 |
| CA | 2474900 | 9/2003 |
| CA | 2476181 | 9/2003 |
| CA | 2594355 | 7/2006 |
| CA | 2640631 | 8/2007 |
| CN | 1830554 | 9/2006 |
| CN | 100378054 | 4/2008 |
| CN | 101774912 | 7/2010 |
| CN | 102731469 | 12/2013 |
| CN | 104277021 | 1/2015 |
| CN | 105408003 | 3/2016 |
| CN | 104672046 | 1/2017 |
| CN | 107011169 | 8/2017 |
| CN | 107089644 | 8/2017 |
| CN | 107245034 | 10/2017 |
| CN | 207451978 | 6/2018 |
| CN | 110461811 | 11/2019 |
| EP | 0441260 | 8/1991 |
| EP | 1069945 | 5/2003 |
| EP | 3271061 | 1/2018 |
| GB | 1264377 | 2/1972 |
| JP | S6396140 A | 4/1988 |
| JP | 2003071299 | 3/2003 |
| JP | 2016539124 A | 12/2016 |
| KR | 101737711 | 5/2017 |
| PL | 200233 | 12/2008 |
| RS | 20050902 | 4/2008 |
| RS | 49815 | 8/2008 |
| RS | 50337 | 11/2009 |
| RS | 50674 | 6/2010 |
| UA | 81759 | 2/2008 |
| UA | 88147 | 9/2009 |
| WO | WO 9502568 | 1/1995 |
| WO | WO 1999051339 | 10/1999 |
| WO | WO 2001090043 | 11/2001 |
| WO | WO 2006130288 | 12/2006 |
| WO | WO 2013030258 | 3/2013 |
| WO | WO 2015059275 | 4/2015 |
| WO | WO 2017114816 | 7/2017 |
| WO | WO 2017114820 | 7/2017 |
| WO | WO 2017114826 | 7/2017 |
| WO | WO 2017114831 | 7/2017 |
| WO | WO 2018114900 A1 | 6/2018 |
| WO | WO 2019197249 | 10/2019 |
| WO | WO 2020072163 | 4/2020 |
| WO | WO 2020075088 | 4/2020 |

OTHER PUBLICATIONS

PCT International Search Report and Written Opinion in International Appln. No. PCT/IB2021/054554, mailed on Aug. 18, 2021, 9 pages.

CONTACT FEED STREAM WITH AN OXIDATIVE
DEHYDROGENATION (ODH) CATALYST UNDER
ODH CONDITIONS IN AN ODH REACTOR

302

300a

LIMITING ACETIC ACID PRODUCTION IN ETHANE ODH PROCESS

CLAIM OF PRIORITY

This application is a National Stage Application under 35 U.S.C. § 371 and claims the benefit of International Application No. PCT/IB2021/054554, filed May 25, 2021, which claims priority to U.S. Provisional Application No. 63/036,471 filed on Jun. 9, 2020, wherein the entire contents of both are hereby incorporated by reference.

TECHNICAL FIELD

The present specification is directed to an oxidative dehydrogenation process to convert ethane to ethylene. More specifically, an oxidative dehydrogenation process which includes acetic acid in the feed stream is described.

BACKGROUND ART

Oxidative dehydrogenation of ethane using mixed metal oxide catalysts is an alternative to steam cracking for the production of ethylene. Oxidative dehydrogenation of ethane is a way of converting ethane, which is relatively inert, into ethylene, which is more reactive and can be more valuable. Oxidative dehydrogenation of ethane involves the endothermic removal of hydrogen from ethane and the exothermic oxidation of hydrogen to produce water. However, oxidative dehydrogenation of ethane may also result in production of unwanted by-products, such as acetic acid. It can therefore be beneficial to selectively oxidize hydrogen and minimize the oxidation of ethane in order to maximize the production of the desired product, ethylene.

SUMMARY OF INVENTION

Certain aspects of the subject matter described can be implemented as a process for the oxidative dehydrogenation (ODH) of ethane. The process includes contacting a feed stream including ethane, oxygen, and acetic acid with an oxidative dehydrogenation catalyst in a oxidative dehydrogenation reactor under oxidative dehydrogenation conditions to produce a product stream including ethylene, unreacted ethane, water, and acetic acid. The concentration of acetic acid in the feed stream is from 0.5 to 10 vol % of the feed stream. The feed stream can optionally include an inert diluent. In some cases, the product stream includes carbon monoxide, carbon dioxide, or both.

This, and other aspects, can include one or more of the following features.

The concentration of acetic acid in the feed stream can be from 2 to 5 vol % of the feed stream. The concentration of acetic acid in the feed stream can be greater than 2 vol % of the feed stream. The feed stream to the reactor can include from 0.5 to 10 vol % acetic acid. The feed stream to the reactor can include an oxygen to ethane molar ratio from 0.5 to 0.7. The feed stream to the reactor can include water ($H_2O$) and carbon dioxide ($CO_2$) in a molar ratio such that the feed composition is outside the flammability limits.

The process can include a downstream separation process. The product stream can be separated, for example, by the downstream separation process, into a liquid stream and a gaseous components stream. The liquid stream can include water and acetic acid. The gaseous components stream can include ethylene and unreacted ethane. In some cases, the gaseous components stream includes carbon monoxide, carbon dioxide, or both. At least a portion of the liquid stream can be recycled to the reactor as part of the feed stream. The liquid stream can be diluted with water to achieve the desired amount of acetic acid in the feed stream. A split fraction of the liquid stream can be adjusted to achieve the desired amount of acetic acid in the feed stream.

The reactor can operate at a temperature from 300° C. to 425° C. The reactor can operate at a temperature from 315° C. to 400° C. The reactor can operate at a pressure from 0.5 psig to 100 psig. The reactor can operate at a pressure from 15 psig to 50 psig.

The gas hourly space velocity (GHSV) of the product stream can be from 500 $h^{-1}$ to 30000 $h^{-1}$. The GHSV of the product stream can be from 1000 $h^{-1}$ to 150000 $h^{-1}$. The GHSV of the product stream can be from 500 $h^{-1}$ to 4000 $h^{-1}$.

The catalyst can include one or more catalysts selected from the group consisting of:
  i) catalysts of the formula:

$$Mo_aV_bTe_cNb_dPd_eO_f$$

where: a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;
  ii) catalysts of the formula:

$$Mo_aE_kG_lO_f$$

where: E is selected from the group consisting of Ba, Ca, Cr, Mn, Nb, Ta, Ti, Te, V, W and mixtures thereof; G is selected from the group consisting of Bi, Ce, Co, Cu, Fe, K, Mg, V, Ni, P, Pb, Sb, Si, Sn, Ti, U, and mixtures thereof; a=1; k is 0 to 2; 1=0 to 2, with the proviso that the total value of 1 for Co, Ni, Fe and mixtures thereof is less than 0.5; and f is a number to satisfy the valence state of the catalyst;
  iii) catalysts of the formula:

$$V_mMo_nNb_oTe_pMe_qO_f$$

where: Me is a metal selected from the group consisting of Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and
  iv) catalysts of the formula:

$$Mo_aV_rX_sY_tZ_uM_vO_f$$

where: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

The liquid stream can include less than 10 vol % of acetic acid.

The selectivity to ethylene can be from 75% to 99%. The selectivity to $CO_2$ can be equal or less than 10%. The selectivity to CO can be equal to or less than 11%. The feed stream to the reactor can include from 2 to 3 vol % of acetic acid, 29 to 57 vol % of $H_2O$, 16 to 26 vol % of $C_2H_6$, 8 to 14 vol % of $O_2$, and 17 to 28 vol % of $CO_2$.

A makeup stream and the gaseous components stream can be contacted with a second oxidative dehydrogenation catalyst under oxidative dehydrogenation conditions in a second oxidative dehydrogenation reactor to produce a second product stream. The second product stream can include ethylene, unreacted ethane, water, and acetic acid. In some cases, the second product stream includes carbon monoxide, carbon dioxide, or both. An overall concentration of acetic acid of the makeup stream and the gaseous components stream (together) entering the second oxidative dehydrogenation reactor can be from 0.5 to 10 vol %.

The process can include a second downstream separation process. The second product stream can be separated, for example, by the second downstream separation process, into a second liquid stream and a second gaseous components stream. The second liquid stream can include water and acetic acid. The second gaseous components stream can include ethylene and unreacted ethane. In some cases, the second gaseous components stream includes carbon monoxide, carbon dioxide, or both. At least a portion of the second liquid stream can be recycled to the reactor as part of the feed stream. The second liquid stream can be diluted with water to achieve the desired amount of acetic acid in the feed stream. A split fraction of the second liquid stream can be adjusted to achieve the desired amount of acetic acid in the feed stream. At least a portion of the second liquid stream can be recycled to the second reactor as part of the makeup stream. The second liquid stream can be diluted with water to achieve the desired amount of acetic acid in the makeup stream. A split fraction of the second liquid stream can be adjusted to achieve the desired amount of acetic acid in the makeup stream.

It is understood that the disclosure described in this specification is not limited to the examples summarized in this Summary. Various other aspects are described and exemplified herein.

DESCRIPTION OF EMBODIMENTS

Figure 1:
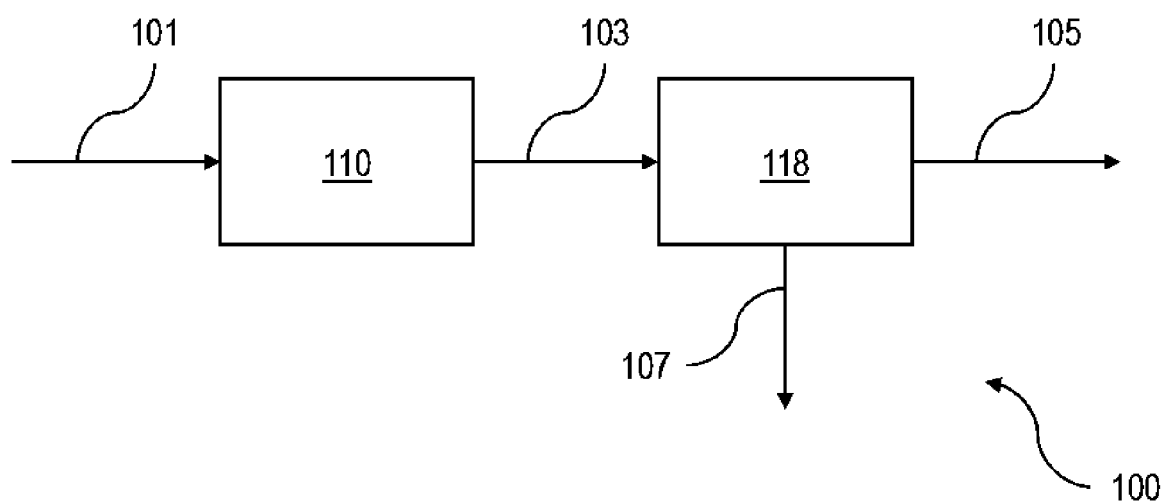
FIG. 1 is a schematic diagram of an example system that includes an oxidative dehydrogenation reactor.

Certain exemplary aspects of the present disclosure will now be described to provide an overall understanding of the principles of the process disclosed herein. Those of ordinary skill in the art will understand that the processes described herein are non-limiting exemplary aspects and that the scope of the various examples of the present disclosure is defined solely by the claims. The features illustrated or described in connection with one exemplary aspect may be combined with the features of other aspects. Such modifications and variations are intended to be included within the scope of the present disclosure.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Definitions

As used herein, the term "oxidative dehydrogenation catalyst" refers to catalysts used in the oxidative dehydrogenation of ethane into ethylene. The most frequently described oxidative dehydrogenation catalysts are mixed metal oxide catalysts. Use of the term "catalyst", unless otherwise indicated, is synonymous with oxidative dehydrogenation catalyst. Furthermore, referral to an oxidative dehydrogenation catalyst can include a mixture of more than one oxidative dehydrogenation catalyst, each having different chemical compositions which can be supported or unsupported.

As used herein, the term "feed stream" refers to the gas stream that initially contacts the oxidative dehydrogenation catalyst. The feed stream in a typical oxidative dehydrogenation process includes the components ethane and oxygen, and possibly one or more inert diluents. In some instances, the contribution of components to the feed stream is described as the "feed composition", where the vol % of one or more components are stated. In some instances, components within the feed stream, particularly oxygen and ethane, are described using a vol % ratio.

As used herein, the term "inert diluent" refers to a gaseous composition that is used to dilute the ethane and oxygen. An inert diluent should primarily exist in the gaseous state under oxidative dehydrogenation conditions and should not increase the flammability of the ethane. Common inert diluents known to the person of ordinary skill in the art for oxidative dehydrogenation include, but are not limited to, nitrogen, carbon dioxide, and steam, and mixtures thereof.

As used herein, the term "under oxidative dehydrogenation conditions" refers to the process conditions that permit conversion, through contact with the oxidative dehydrogenation catalyst in the presence of oxygen, of ethane into ethylene, and includes, but is not limited to, temperature, pressure, and the flow rate of the feed stream. Oxidative dehydrogenation conditions can be adjusted by the person of ordinary skill in the art in an attempt to optimize conditions for a particular catalyst or whether an inert diluent is used in the feed stream.

As used herein, the term "selectivity", unless otherwise indicated, refers to the carbon atom selectivity, based on the degree to which ethane is consumed. Selectivity, stated as a %, can be calculated according to the formula:

$$\text{Selectivity } (\%) = \left[ \frac{\frac{\text{Net mass flow rate of } X \, (g\,X/\text{min})}{\text{Molecular weight of } X \, (g\,X/\text{mol}\,X)}}{\frac{\text{Net mass flow rate of converted } C_2H_6 \, (g\,C_2H_6/\text{min})}{\text{Molecular weight of } C_2H_6 \, (g\,C_2H_6/\text{mol }C_2H_6)} * \frac{\text{Mol. Equiv. of } X}{\text{mol } C_2H_6}} \right] * 100$$

where X is the product that is being assessed, the net mass flow rate refers to flow in g/min for X or converted $C_2H_6$ and is equal to the mass flow rate of X or converted $C_2H_6$ in the product stream minus the mass flow rate of component X or converted $C_2H_6$ in the feed stream, and molar equivalent (Mol. Equiv.) refers to the amount of X, in moles, that reacts completely with or is produced by one mole of ethane. If the sum of all selectivities for products derived from conversion of ethane did not total 100%, the selectivities are normalized to 100%. Normalization for each product can be calculated by dividing the selectivity for that product by the sum of all carbon atom product selectivities.

As used herein, the term "about" or "approximately" can allow for a degree of variability in a value or range, for example, within 10%, within 5%, or within 1% of a stated value or of a stated limit of a range.

Embodiments of the present techniques are directed to a process for oxidative dehydrogenation (ODH) of ethane into ethylene, under conditions that limit production of acetic acid. Typically, oxidative dehydrogenation of ethane involves feeding a gas stream including ethane and oxygen, and optionally an inert diluent, into an oxidative dehydrogenation reactor that includes an oxidative dehydrogenation catalyst. Contact of the ethane and oxygen with the oxidative dehydrogenation catalyst results in the formation of ethylene and various by-products, including acetic acid. The production of by-products such as acetic acid results in a need for costly downstream separation of the acetic acid from the target product ethylene. It is an object of the present disclosure to limit the degree to which acetic acid is produced in the oxidative dehydrogenation of ethane by including acetic acid along with ethane and oxygen in the initial feed to the process. Reducing the amount of acetic acid produced can reduce the complexity and size of acetic acid downstream separation infrastructure.

The ODH Process

Provided in this disclosure is a process for the oxidative dehydrogenation of ethane. The process includes contacting a feed stream that includes ethane, oxygen, acetic acid, and optionally an inert diluent, with an oxidative dehydrogenation catalyst under oxidative dehydrogenation conditions in an oxidative dehydrogenation reactor to produce a product stream including ethylene, unreacted ethane, water, acetic acid, and possibly one or both of carbon dioxide and carbon monoxide. The contribution of acetic acid in the feed stream is from 0.5 vol % to 10 vol % of the feed stream. The system 100 of FIG. 1 can implement the oxidative dehydrogenation process.

Feed Composition

The present disclosure, in one aspect, seeks to limit the production of acetic acid in a process of oxidative dehydrogenation of ethane by including acetic acid in the feed stream 101. Depending upon process conditions and the nature of the oxidative dehydrogenation catalyst, the selectivity of acetic acid using a traditional feed stream without acetic acid can vary widely, but an experienced operator should be able to limit selectivity of acetic acid to below 10% of the converted ethane. By including acetic acid in the feed stream 101 the selectivity to acetic acid can be reduced. It was found that by including from 0.5 vol % up to 10 vol % of acetic acid in the feed stream 101 that the formation of acetic acid was partially or completely suppressed. In addition, it was found that negative selectivity for acetic acid is possible, where the amount of acetic acid in the product stream 103 is reduced compared to the amount of acetic acid in the feed stream 101. In some embodiments, the amount of acetic acid in the feed stream 101 is from 1 vol % to 10 vol %, or from 2 vol % to 5 vol %. In some embodiments, the amount of acetic acid in the feed stream 101 is about 0.5 vol %, about 1 vol %, about 1.5 vol %, about 2 vol %, about 2.5 vol %, about 3 vol %, about 3.5 vol %, about 4 vol %, about 4.5 vol %, about 5 vol %, about 6 vol %, about 7 vol %, about 8 vol %, about 9 vol %, or about 10 vol %. In some embodiments, the amount of acetic acid in the feed stream 101 is about 3 vol %.

The process of oxidative dehydrogenation of ethane falls within the skill of the ordinary person in the art. The feed preferably includes an $O_2$:$C_2H_6$ ratio that falls outside of flammability limits to prevent process upsets. A user can determine how much inert diluent, such as carbon dioxide and water (in the form of steam), or mixtures thereof, can be added to ensure the mixture is outside the flammability limits. It should be noted that a feed stream 101 without an inert diluent, while possible, would not be ideal as to remain outside the flammability limit the feed stream would require an $O_2$:$C_2H_6$ ratio that is very small, or extremely high. Use of steam as an inert diluent provides the advantage of being simpler to separate from the gaseous target products, but is known to also increase selectivity to acetic acid. Including acetic acid in the feed stream 101 can allow for the use of steam as the inert diluent and for the simpler separation from the target products while minimizing or even avoiding the increase in selectivity to acetic acid.

In some embodiments, the $O_2$:$C_2H_6$ volume ratio in the feed stream 101 is from 0.2:1 to 1:1, from 0.3:1 to 0.8:1, or from 0.4:1 to 0.7:1. In some embodiments, the contribution of ethane in the feed stream 101 is from 10 vol % to 80 vol %, from 12 vol % to 50 vol %, or from 15 vol % to 30 vol %. In some embodiments, the contribution of oxygen in the feed stream 101 is from 1 vol % to 30 vol %, from 5 vol % to 25 vol %, or from 8 vol % to 18 vol %.

The components of the feed stream 101 can be premixed before introduction into the oxidative dehydrogenation reactor 110 or the components may be added separately to the oxidative dehydrogenation reactor 110. It is also contemplated that some components are premixed and some components are separately fed to the oxidative dehydrogenation reactor 110. For example, ethane can be saturated with the inert diluent and introduced into the reactor 110 while the oxygen is added separately. The ethane saturated with the inert diluent can then be combined with the oxygen to form the feed stream 101 that contacts the catalyst. The process described also contemplates staged additions of components into a gas stream, each stage contributing another component to the gas stream with the feed stream 101 being formed after the last component is added. In the process of oxidative dehydrogenation described herein, the feed stream 101 introduced into the oxidative dehydrogenation reactor 110 includes acetic acid, in addition to ethane, oxygen, and optionally one or more inert diluents.

The acetic acid may be added separately to the oxidative dehydrogenation reactor 110 or may be mixed with one or more of the ethane, oxygen, or inert diluent. Acetic acid may be added as glacial acetic acid or in a diluted form to provide acetic acid in amounts ranging from about 0.5 to 10.0 vol % of the feed stream 101. Use of dilute aqueous acetic acid is ideal as water is well known as being suitable for use as the inert diluent in the oxidative dehydrogenation process.

The feed stream 101 can be heated, at a minimum, to a temperature above the dew point of the feed stream 101 to ensure all components are in a gaseous state before making contact with the oxidative dehydrogenation catalyst. This is particularly relevant when water is employed as inert diluent because the oxidative dehydrogenation catalyst may be sensitive to liquid water, but not steam. The components may be heated separately or as a complete mixture. In some embodiments, the temperature of the feed stream 101 is at least 150° C., at least 225° C., or at least 300° C.

The temperature of the feed stream 101, or individual components, upon entering the reactor 110 may be lower than 150° C. provided that before contact with the catalyst the temperature is increased to above the dew point. In this instance, a portion of the reactor 110 may be used to heat the feed stream components to the preferred temperature. This portion of the catalyst bed may be loaded with heat conductive non-catalytic material.

Reactor

Any of the known reactor types applicable for the oxidative dehydrogenation of hydrocarbons can be used with the present techniques. Particularly suited for use are conventional fixed bed reactors. In a typical fixed bed reactor, reactants are introduced into the reactor at one end, flow past an immobilized catalyst, products are formed and leave at the other end of the reactor. Designing a suitable fixed bed reactor may follow techniques known for reactors of this type. A person skilled in the art would know which features are required with respect to shape and dimensions, inputs for reactants, outputs for products, temperature and pressure control, and means for immobilizing the catalyst. In some embodiments, the oxidative dehydrogenation reactor 110 includes a fixed bed reactor.

A fluidized bed reactor can also be used. These types of reactors are also well known. Typically, the catalyst is supported by a porous structure, or distributor plate, located near a bottom end of the reactor, and reactants flow through at a velocity sufficient to fluidize the bed (e.g., the catalyst rises and begins to swirl around in a fluidized manner). The reactants are converted to products upon contact with the fluidized catalyst and subsequently removed from the upper end of the reactor. Design considerations include shape of the reactor and distributor plate, input and output, and temperature and pressure control, all of which would fall under knowledge of the person skilled in the art. In some embodiments, the oxidative dehydrogenation reactor 110 includes a fluidized bed reactor.

Various tools commonly used for chemical reactors, including flowmeters, compressors, valves, and sensors for measuring parameters such as temperature and pressure can be used. It is expected that the person of ordinary skill in the art would include these components as deemed necessary for operation or for compliance with legal obligations related to safety regulations.

Process Conditions

Use of an oxidative dehydrogenation reactor 110 for performing an oxidative dehydrogenation of ethane process consistent with the present disclosure falls within the knowledge of the person skilled in the art. An operator may alter the process conditions, along with the feed composition, to optimize product selectivity, conversion, and or yield.

It is well known that catalyst beds may have a temperature profile or gradient that can vary according to reactor type, process conditions and catalyst composition. Measuring or estimating the temperature of the catalyst bed is also well known in the art, including measuring the temperature at single or multiple points within the catalyst bed. If the variation of temperature within the catalyst bed is minimal, ranging no more than 25° C., preferably no more than 10° C., the temperature may measured at a single point. Preferably, the temperature of the catalyst is calculated using a weight-averaged bed temperature using 3 or more points within the bed. In some embodiments, the oxidative dehydrogenation of ethane may be conducted at temperatures from 300° C. to 450° C., from 315° C. to 425° C., or from 330° C. to 400° C. In some embodiments, the oxidative dehydrogenation of ethane may be conducted at temperatures of about 300° C., about 315° C., about 330° C., about 400° C., about 425° C., or about 450° C.

Operating pressure may also be controlled by an operator, including the inlet pressure at which the feed stream is introduced into the oxidative dehydrogenation reactor, the inlet pressure being higher than the outlet pressure due to a pressure drop through the length of the catalyst bed. Pressures described are for inlet pressure. In some embodiments, the oxidative dehydrogenation of ethane may be conducted at pressures from 0.5 to 100 psig (3.447 to 689.47 kPag) or from 15 to 50 psig (103.4 to 344.73 kPag). In some embodiments, the oxidative dehydrogenation of ethane may be conducted at pressures of about 0.5 psig, about 10 psig, about 15 psig, about 20 psig, about 30 psig, about 50 psig, about 75 psig, or about 100 psig.

In some embodiments, the residence time of the ethane in the reactor 110 is from 0.002 to 30 seconds or from 1 to 10 seconds. In some embodiments, the residence time of the ethane in the reactor 110 is about 0.002 seconds, about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, or about 30 seconds. The flow of reactants and inert diluent can be described in any number of ways known in the art. Typically, flow is described and measured in relation to the volume of all feed gases (reactants and diluent) that pass over the volume of the active catalyst bed in one hour, or gas hourly space velocity (GHSV). In some embodiments, the GHSV is from 500 to 30000 $h^{-1}$, from 1000 $h^{-1}$ to 20000 $h^{-1}$, from 1500 $h^{-1}$ to 10000 $h^{-1}$, or from 2000 $h^{-1}$ to 10000 $h^{-1}$. In some embodiments, the GHSV is about 500 $h^{-1}$, about 1000 $h^{-1}$, about 1500 $h^{-1}$, about 2000 $h^{-1}$, about 3000 $h^{-1}$, about 4000 $h^{-1}$, about 5000 $h^{-1}$, about 6000 $h^{-1}$, about 7000 $h^{-1}$, about 8000 $h^{-1}$, about 9000 $h^{-1}$, about 10000 $h^{-1}$, about 15000 $h^{-1}$, about 20000 $h^{-1}$, about 25000 $h^{-1}$, or about 30000 $h^{-1}$.

The flow rate can also be measured as weight hourly space velocity (WHSV), which describes the flow in terms of the weight, as opposed to volume, of the gases that flow over the weight of the active catalyst per hour. In calculating WHSV the weight of the gases may include only the reactants but may also include diluents added to the gas mixture. In some embodiments, the WHSV, including the weight of diluents, is from 0.5 $h^{-1}$ to 50 $h^{-1}$, from 1.0 to 25.0 $h^{-1}$, or from 2.0 to 10.0 $h^{-1}$. In some embodiments, the WHSV, including the weight of diluents, is about 0.5 $h^{-1}$, about 1.0 $h^{-1}$, about 1.5 $h^{-1}$, about 2.0 $h^{-1}$, about 3.0 $h^{-1}$, about 4.0 $h^{-1}$, about 5.0 $h^{-1}$, about 6.0 $h^{-1}$, about 7.0 $h^{-1}$, about 8.0 $h^{-1}$, about 9.0 $h^{-1}$, about 10 $h^{-1}$, about 15 $h^{-1}$, about 20 $h^{-1}$, about 25 $h^{-1}$, about 30 $h^{-1}$, about 40 $h^{-1}$, or about 50 $h^{-1}$.

The flow of the feed stream 101 through the reactor 110 may also be described as the linear velocity of the feed stream (cm/s), which is defined in the art as the flow rate of the feed stream 101/cross-sectional surface area of the reactor 110/void fraction of the catalyst bed. The flow rate generally means the total of the flow rates of all the gases entering the reactor 110, and is measured where the oxygen and alkane first contact the catalyst and at the temperature and pressure at that point. The cross-section of the reactor 110 is also measured at the entrance of the catalyst bed. The void fraction of the catalyst bed is defined as the volume of voids in the catalyst bed/total volume of the catalyst bed.

The volume of voids refers to the voids between catalyst particles and does not include the volume of pores inside the catalyst particles. In some embodiments, the linear velocity is from 5 cm/sec to 1500 cm/sec, from 10 cm/sec to 500 cm/sec, or from 25 cm/sec to 350 cm/sec. In some embodiments, the linear velocity is about 5 cm/sec, about 10 cm/sec, about 15 cm/sec, about 20 cm/sec, about 25 cm/sec, about 50 cm/sec, about 75 cm/sec, about 100 cm/sec, about 150 cm/sec, about 200 cm/sec, about 250 cm/sec, about 300 cm/sec, about 350 cm/sec, about 400 cm/sec, about 500 cm/sec, about 600 cm/sec, about 700 cm/sec, about 800 cm/sec, about 900 cm/sec, about 1000 cm/sec, about 1250 cm/sec, or about 1500 cm/sec. In some embodiments, the space-time yield of ethylene (productivity) in g of ethylene/hour per kg of the catalyst is at least 900 $h^{-1}$ or at least 1500 $h^{-1}$. In some embodiments, the space-time yield of ethylene (productivity) in g of ethylene/hour per kg of the catalyst is at least 3500 $h^{-1}$, when the temperature is from 350° C. to 400° C. It should be noted that the increased productivity of the catalyst with increasing temperature is usually accompanied by a decrease in selectivity to ethylene.

Optimization or adjustment of the process conditions can impact the conversion rates of ethane and corresponding selectivities, including selectivity for ethylene and acetic acid. In some embodiments, the process has a selectivity for ethylene of at least 60%, at least 75%, or at least 90%. In some embodiments, the conversion of ethane is at least 25%, at least 40%, at least 50%, at least 60%, or at least 70%.

Catalysts

There are a number of known catalysts which may be used in the oxidative dehydrogenation of ethane. Mixed metal oxides including molybdenum and vanadium are particularly well suited for implementation in the catalyst. Typically, the oxidative dehydrogenation catalysts comprise a mixed metal oxide catalysts selected from the group consisting of:

i) catalysts of the formula:

$$Mo_aV_bTe_cNb_dPd_eO_f$$

wherein: a, b, c, d, e and f are the relative atomic amounts of the elements Mo, V, Te, Nb, Pd and O, respectively; and when a=1, b=0.01 to 1.0 preferably 0.1 to 0.4, c=0.01 to 1.0 preferably 0.1 to 0.3, d=0.01 to 1.0 preferably 0.1 to 0.3, 0.00≤e≤0.10 preferably from 0.03 to 0.1 and f is a number to satisfy the valence state of the catalyst;

ii) catalysts of the formula:

$$Mo_aE_kG_lO_f$$

wherein: E is selected from the group consisting of Ba, Ca, Cr, Mn, Nb, Ta, Ti, Te, V, W and mixtures thereof; G is selected from the group consisting of Bi, Ce, Co, Cu, Fe, K, Mg, V, Ni, P, Pb, Sb, Si, Sn, Ti, U, and mixtures thereof; a=1; k is 0 to 2, preferably 0.2 to 0.6; l=0 to 2, preferably 0.2 to 0.6, with the proviso that the total value of l for Co, Ni, Fe and mixtures thereof is less than 0.5; and f is a number to satisfy the valence state of the catalyst;

iii) catalysts of the formula:

$$V_mMo_nNb_oTe_pMe_qO_f$$

wherein: Me is a metal selected from the group consisting of Ta, Ti, W, Hf, Zr, Sb and mixtures thereof; m is from 0.1 to 3, in some instances from 0.5 to 1; n is from 0.5 to 1.5, in some instances from 0.5 to 1; o is from 0.001 to 3 in some instances from 0.01 to 1; p is from 0.001 to 5 in some instances from 0.01 to 1; q is from 0 to 2 in some instances from 0.01 to 1; and f is a number to satisfy the valence state of the catalyst; and iv) catalysts of the formula:

$$MO_aV_rX_sZ_uM_vO_f$$

wherein: X is at least one of Nb and Ta; Z is at least one of Te, Ga, Pd, W, Bi and Al, in some embodiments Te, Pd, W, and Bi; M is at least one of Fe, Co, Cu, Cr, Ti, Ce, Zr, Mn, Pb, Mg, Sn, Pt, Si, La, K, Ag and In in some instances Fe, Co, Cu, Cr, Ti, Ce, Zr, Mn, Mg, Sn, Pt, La, Ag and In; a=1.0 (normalized); r=0.05 to 1.0 in some embodiments 0.05 to 0.5; s=0.001 to 1.0 in some embodiment 0.01 to 0.4; t=0.001 to 1.0 in some embodiment from 0.01 to 0.4; u=0.001 to 0.5 in some embodiments 0.01 to 0.03; v=0.001 to 0.3 in some embodiments from 0.01 to 0.2; and f is a number to satisfy the valence state of the catalyst.

In some embodiments, the catalyst is a catalyst that includes molybdenum, vanadium, tellurium, niobium, and oxygen wherein the molar ratio of molybdenum to vanadium is from 1:0.12 to 1:0.49, the molar ratio of molybdenum to tellurium is from 1:0.01 to 1:0.30, the molar ratio of molybdenum to niobium is from 1:0.01 to 1:0.30, and oxygen is present at least in an amount to satisfy the valency of any present metal oxides.

In some embodiments, the catalyst is a catalyst that includes molybdenum, vanadium, tellurium, niobium, and oxygen wherein the molar ratio of molybdenum to vanadium is from 1:0.20 to 1:0.45, the molar ratio of molybdenum to tellurium is from 1:0.05 to 1:0.25, the molar ratio of molybdenum to niobium is from 1:0.05 to 1:0.25, and oxygen is present at least in an amount to satisfy the valency of any present metal oxides.

In some embodiments, the catalyst is a catalyst that includes molybdenum, vanadium, tellurium, niobium, and oxygen wherein the molar ratio of molybdenum to vanadium is from 1:0.25 to 1:0.40, the molar ratio of molybdenum to tellurium is from 1:0.10 to 1:0.20, the molar ratio of molybdenum to niobium is from 1:0.10 to 1:0.20, and oxygen is present at least in an amount to satisfy the valency of any present metal oxides.

In some embodiments, the catalyst is a catalyst that includes molybdenum, vanadium, tellurium, niobium, and oxygen wherein the molar ratio of molybdenum to vanadium is from 1:0.30 to 1:0.35, the molar ratio of molybdenum to tellurium is from 1:0.13 to 1:0.17, the molar ratio of molybdenum to niobium is from 1:0.12 to 1:0.14, and oxygen is present at least in an amount to satisfy the valency of any present metal oxides.

Recycling Acetic Acid

In another aspect of the present disclosure, acetic acid produced in the oxidative dehydrogenation of ethane process can be recovered and recycled for addition to the feed stream. The product stream may undergo processing steps to isolate the target product ethylene. It has been described in the art that a first processing step ideally involves removing acetic acid and water from the product stream, typically including cooling the product stream to condense a significant portion of the acetic acid and steam which can subsequently be easily separated from the gaseous components as a liquid stream 107. The gaseous components form part of a gaseous components stream 105 including ethane, ethylene, and carbon dioxide, which may then be subjected to further processing steps, which may include separating carbon dioxide from the ethane and ethylene, followed by separation of ethane from ethylene. Isolated ethane can be recycled to form part of the feed stream 101. Cooling and separation of acetic acid from the product stream 103 can be non-dilutive, for example, by passing the product stream 103 through a heat exchanger. Cooling and separation of acetic acid from the product stream 103 can be dilutive, for example, by introducing the product stream 103 into a quench tower 118 where cold water is added to the stream 103. A combination of methods may also be employed. Regardless of which method is used for separation (dilutive, non-dilutive, or a combination of both) the liquid stream 107 including aqueous acetic acid can be recycled for use in the feed stream 101.

The concentration of acetic acid in the liquid stream 107 can vary depending upon the original concentration in the product stream 103 and what method or combination of methods are used for separation. For example, dilutive cooling using a quench tower 118 will result in a much lower concentration of acetic acid due to the addition of water during quenching. A person skilled in the art would be able to determine the concentration of acetic acid in the liquid stream 107 and subsequently extrapolate how much of the liquid stream 107 can be recycled to the feed stream 101 to provide 0.5 to 10 vol % of acetic acid. In instances where not all of the liquid stream 107 is required to provide the desired vol % of acetic acid in the feed stream 101, a split fraction of the liquid stream 107 can be recycled for addition to the feed stream 101 and the remainder may be sent for further processing, such as upgrading to glacial acetic acid, using methods known in the art. In instances where the concentration of acetic acid in the liquid stream 107 is insufficient to provide enough acetic acid to provide 0.5 vol % to 10 vol % in the feed stream an additional source of acetic acid can be utilized to make up the difference. The gaseous portions of the streams 101, 103, and 105 have compositions outside of their respective flammability limits.

Figure 2A:
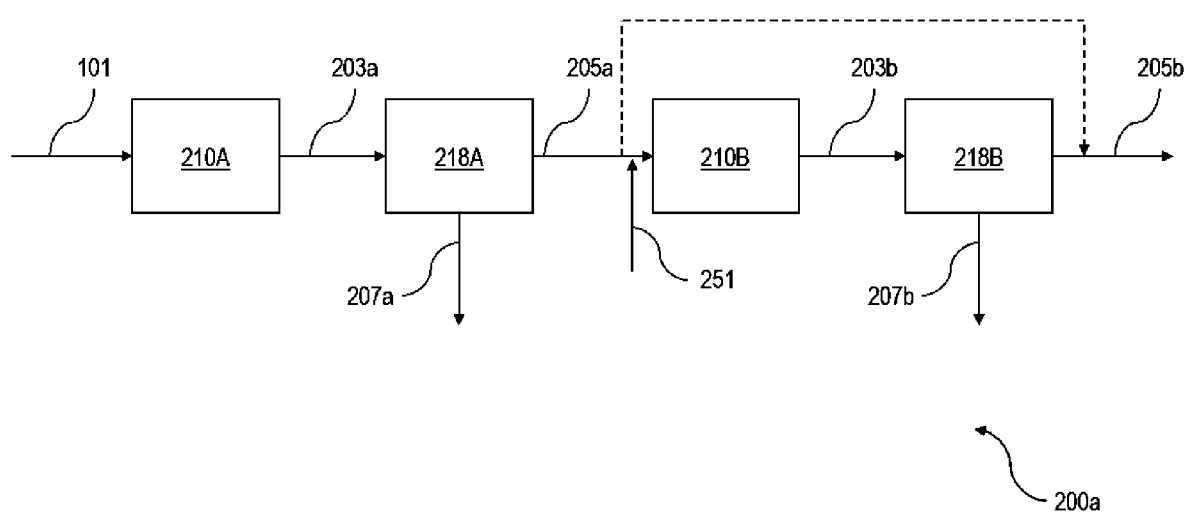
FIG. 2A is a schematic diagram of an example system that includes two implementations of the oxidative dehydrogenation reactor of FIG. 1.
Figures 2B, 3A:
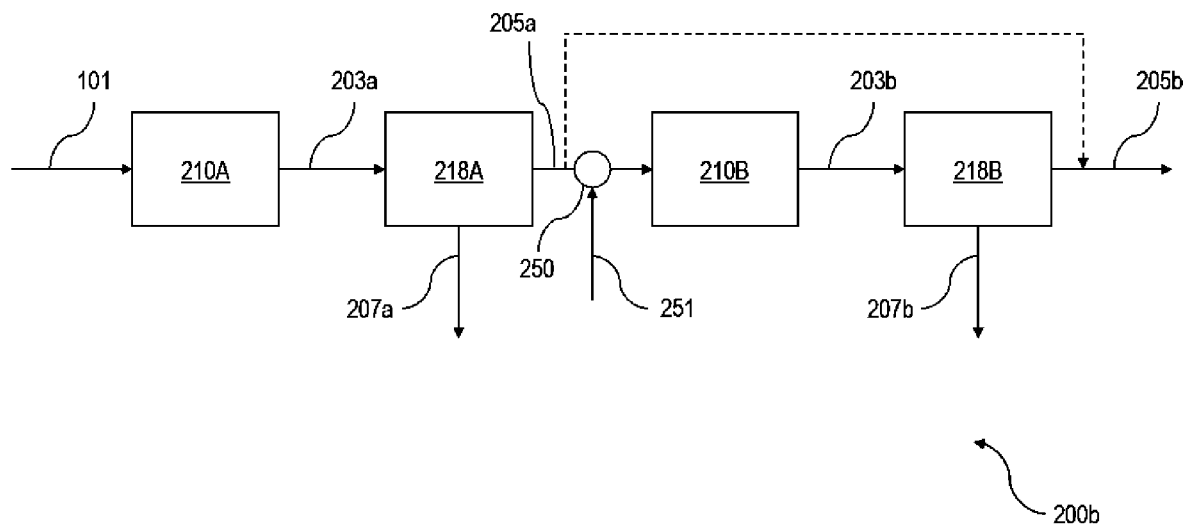
FIG. 2B is a schematic diagram of an example system that includes two implementations of the oxidative dehydrogenation reactor of FIG. 1.
FIG. 3A is a flow chart of an example method for an oxidative dehydrogenation process.

In some embodiments, the oxidative dehydrogenation of hydrocarbons is performed using multiple implementations of the ODH reactor 110 (examples shown in FIGS. 2A and 2B). The reactors can be in a parallel flow configuration, a serial flow configuration, or a combination of these. As shown in FIG. 2A, the oxidative dehydrogenation of hydrocarbons can be performed by a system 200a that includes two oxidative dehydrogenation reactors 210A, 210B in a serial flow configuration. Each of the ODH reactors 210A and 210B are implementations of the ODH reactor 110 described previously. The feed stream 101 flows to ODH reactor 210A and comes into contact with the catalyst in the ODH reactor 210A.

Product stream 203a flows from the ODH reactor 210A to a quench tower 218A, where acetic acid is separated from the product stream 203a. Liquid stream 207a, including acetic acid, flows out of the quench tower 218A. The gaseous components stream 205a flows from the quench tower 218A to the ODH reactor 210B and comes into contact with the catalyst in the ODH reactor 210B. In some embodiments, a makeup stream 251 flows to the ODH reactor 210B and comes into contact with the catalyst in the ODH reactor 210B. In some embodiments, the makeup stream 251 has the same composition as the feed stream 101. In some embodiments, the makeup stream 251 has the same components as the feed stream 101 but may differ in quantities of each component from the feed stream 101. In some embodiments, the composition and flow rate of the makeup stream 251 is determined, such that the overall flow (gaseous components stream 205a and makeup stream 251 together) entering the ODH reactor 210B has the same composition as the feed stream 101. The components of the gaseous components stream 205a and the makeup stream 251 can be premixed before introduction into the ODH reactor 210B, or the components may be added separately to the ODH reactor 210B. It is also contemplated that some components are premixed and some components are separately fed to the ODH reactor 210B.

Product stream 203b flows from the ODH reactor 210B to a quench tower 218B, where acetic acid is separated from the product stream 203b. Liquid stream 207b, including acetic acid, flows out of the quench tower 218B. The gaseous components stream 205b flows out of the quench tower 210B. The compositions of the feed stream 101 and the makeup stream 251 can be adjusted, such that the overall flows entering each of the ODH reactors 210A, 210B have an acetic acid content in a range of from 0.5 vol % to 10 vol %. The compositions of the feed stream 101 and the makeup stream 251 can be adjusted, such that the gaseous portions of the streams 101, 203a, 203b, 205a, 205b, and 251 have compositions outside of their respective flammability limits. In some embodiments, the composition of the feed stream 101, the operating temperature of the ODH reactor 210A, the operating pressure of the ODH reactor 210A, the composition of the makeup stream 251, the amount of the gaseous components stream 205a that splits and bypasses the ODH reactor 210B, or a combination of these are adjusted, such that ethylene content of the overall flow entering the ODH reactor 210B is equal to or less than 20 weight %.

In some embodiments, a portion of the gaseous components stream 205a splits and bypasses the ODH reactor 210B and quench tower 218B and combines with the gaseous components stream 205b. The gaseous component stream 205b (and in some cases, a portion of the gaseous components stream 205a that has combined with 205b), including ethane, ethylene, and carbon dioxide, may then be subjected to further processing steps, which may include separating carbon dioxide from the ethane and ethylene, followed by separation of ethane from ethylene. In some embodiments, the liquid stream 207a, the liquid stream 207b, or both liquid streams 207a, 207b are recycled to form at least a part of the feed stream 101. In some embodiments, the liquid stream 207a, the liquid stream 207b, or both liquid streams 207a, 207b are recycled to form at least a part of the makeup stream 251.

The operating conditions (temperature and pressure) of the ODH reactors 210A, 210B can be adjusted to improve control of product distribution, increase net ethylene yield, reduce the amount of diluent gas used in the ODH process, or any combination of these. For example, the upstream ODH reactor 210A can operate at a decreased temperature in comparison to the downstream ODH reactor 210B, an increased temperature in comparison to the downstream ODH reactor 210B, or the same temperature as the downstream ODH reactor 210B. For example, the upstream ODH reactor 210A can operate at a decreased pressure in comparison to the downstream ODH reactor 210B, an increased pressure in comparison to the downstream ODH reactor 210B, or the same pressure as the downstream ODH reactor 210B. In embodiments where the upstream ODH reactor 210A operates at a decreased pressure in comparison to (or the same pressure as) the downstream ODH reactor 210B, the system 200b can include an ejector 250, as shown in FIG. 2B. In such embodiments, the makeup stream 251 can be used as the motive fluid by the ejector 250. The makeup stream 251 and the gaseous components stream 205a mix as they flow through the ejector 250, and the mixture flows from the ejector 250 to the ODH reactor 210B. The operating conditions of the motive fluid (makeup stream 251) to the ejector 250 can be adjusted accordingly to meet the target operating conditions of the ODH reactor 210B. Similarly, the operating conditions of the feed stream 101 can be adjusted accordingly to meet the target operating conditions of the ODH reactor 210A.

Referring to FIG. 3A, method 300a can be implemented for an oxidative dehydrogenation process. The method 300a can, for example, be implemented by any of the systems 100, 200a, or 200b. At step 302, a feed stream (such as feed stream 101) is contacted with an oxidative dehydrogenation catalyst under oxidative dehydrogenation conditions in an oxidative dehydrogenation reactor (such as the ODH reactor 110, 210A, or 210B). As mentioned previously, the feed stream 101 includes ethane, oxygen, and acetic acid. The concentration of acetic acid in the feed stream 101 is from 0.5 to 10 vol % of the feed stream 101. In some cases, the feed stream 101 includes additional components, such as an inert diluent. Contacting the feed stream 101 with the oxidative dehydrogenation catalyst under oxidative dehydrogenation conditions in the ODH reactor (110, 210A, 210B) produces a product stream (such as the product stream 103, 203a, or 203b). As mentioned previously, the product stream (103, 203a, 203b) includes ethylene, unreacted ethane, water, and acetic acid. In some cases, the product stream (103, 203a, 203b) includes additional components, such as carbon monoxide, carbon dioxide, or both.

Figure 3B:
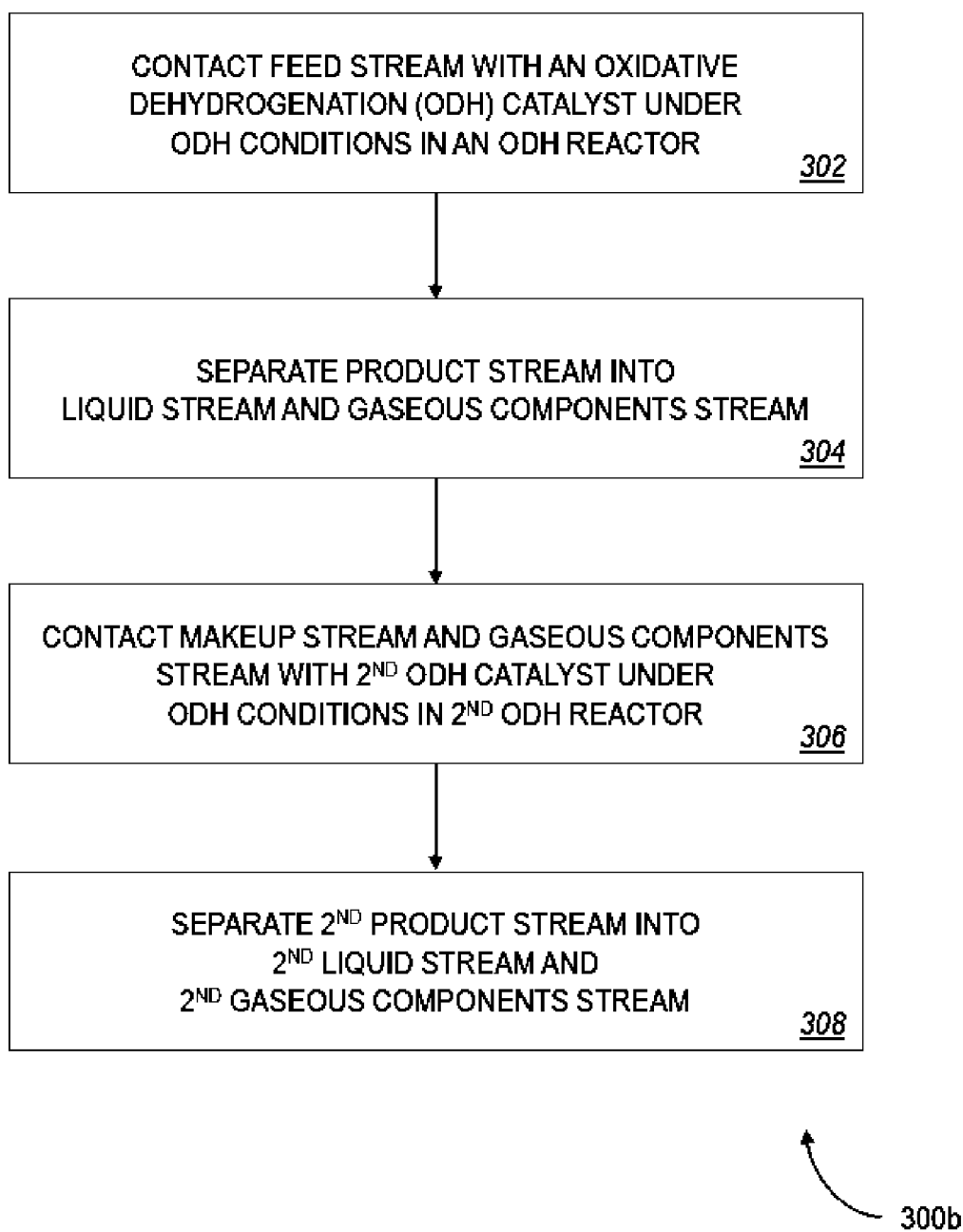
FIG. 3B is a flow chart of an example method for an oxidative dehydrogenation process.

Referring to FIG. 3B, method 300b can be implemented for an oxidative dehydrogenation process. The method 300b can, for example, be implemented by any of the systems 200a or 200b. Similar to method 300a, method 300b includes step 302. At step 304, the product stream 203a is separated into a liquid stream (such as the liquid stream 207a) and a gaseous components stream (such as the gaseous components stream 205a). Step 304 can be implemented by a downstream separation process, such as the quench tower 218A. In some embodiments, at least a portion of the liquid stream 207a is recycled to the ODH reactor 210A as part of the feed stream 101.

At step 306, a makeup stream (such as the makeup stream 251) and the gaseous components stream 205a are contacted with a second oxidative dehydrogenation catalyst under oxidative dehydrogenation conditions in a second oxidative dehydrogenation reactor (such as the ODH reactor 210B). Contacting the makeup stream 251 and the gaseous components stream 205a with the oxidative dehydrogenation catalyst under oxidative dehydrogenation conditions in the ODH reactor 210B produces a second product stream (such as the product stream 203b). As mentioned previously, the product stream 203b includes ethylene, unreacted ethane, water, and acetic acid. In some cases, the product stream 203b includes additional components, such as carbon monoxide, carbon dioxide, or both. An overall concentration of acetic acid of the makeup stream 251 and the gaseous components stream 205a (together) entering the ODH reactor 210B is from 0.5 to 10 vol %. At step 308, the product stream 203b is separated into a second liquid stream (such as the liquid stream 207b) and a second gaseous components stream (such as the gaseous components stream 205b). Step 308 can be implemented by a second downstream separation process, such as the quench tower 218B. In some embodiments, at least a portion of the second liquid stream 207b is recycled to the ODH reactor 210A as part of the feed stream 101 or to the second ODH reactor 210B as part of the makeup stream 251.

Examples

The following examples are merely illustrative of the subject matter of this disclosure and are not intended to be limiting. Computational modeling of an ODH process was used to demonstrate the effect of adding acetic acid to the feed stream on the production of acetic acid. Modeling was on experimental data produced using a catalyst including molybdenum, vanadium, niobium, and tellurium. The model demonstrates the effect of adding acetic acid to the feed stream under ODH process conditions at different temperatures, GHSV, and feed composition. For each process condition a base case of 0 vol % acetic acid in the feed stream was compared to cases with 2 vol %, 5 vol %, and 10 vol % of acetic acid in the feedstream.

Cases 1-5 are modeling examples where each case represents a different process condition or feed composition that is varied and modeled for 0 vol %, 2 vol %, 5 vol %, and 10 vol % of acetic acid in the feed stream. The process conditions and feed composition for each of cases 1 through 5 are summarized in Table 1. The feed stream composition only lists the $O_2$ vol %, $C_2H_6$ vol %, and $CO_2$ vol %, with the balance covering water and acetic acid added to bring the total to 100 vol %. The results, including selectivity for ethylene and acetic acid, and for conversion of ethane (%), for 0 vol %, 2 vol %, 5 vol %, and 10 vol % of acetic acid added to the feed stream, are summarized in Table 2-1, showing that for each vol % of acetic acid in the feed stream there is a decrease in selectivity for acetic acid when compared to when there is no acetic acid in the feed stream. The results for 0.5 vol % of acetic acid in the feed stream, including conversion of ethane and selectivity of ethylene, acetic acid, and carbon monoxide/dioxide, are summarized in Table 2-2 as an intermediate between 0 vol % and 2 vol % of acetic acid in the feed stream, which are shown in Table 2-1. Table 2-2 confirms the trend for selectivity of acetic acid decreasing in the product as acetic acid content in the feed stream increases.

TABLE 1

The Process Conditions and Feed Composition for Each of Cases 1 Through 5.

| | Process Conditions | | | Feed Composition (vol %) | | |
|---|---|---|---|---|---|---|
| Exp. | Temp (° C.) | Pressure (psig) | GHSV ($h^{-1}$) | $O_2$ | $C_2H_6$[1] | $CO_2$ |
| 1-a | 300 | 20 | 1000 | 8 | 16 | 28 |
| 1-c | 370 | 20 | 1000 | 8 | 16 | 28 |
| 1-e | 425 | 20 | 1000 | 8 | 16 | 28 |
| 2-a | 370 | 20 | 500 | 8 | 16 | 28 |
| 2-c | 370 | 20 | 2000 | 8 | 16 | 28 |
| 2-e | 370 | 20 | 10000 | 8 | 16 | 28 |
| 3-a | 370 | 2 | 1000 | 8 | 16 | 28 |
| 3-c | 370 | 14 | 1000 | 8 | 16 | 28 |
| 3-e | 370 | 100 | 1000 | 8 | 16 | 28 |
| 4-a | 370 | 20 | 1000 | 4 | 20 | 28 |
| 4-c | 370 | 20 | 1000 | 8 | 16 | 28 |
| 4-e | 370 | 20 | 1000 | 18 | 18 | 28 |
| 5-a | 370 | 20 | 1000 | 18 | 36 | 0 |
| 5-b | 370 | 20 | 1000 | 8 | 16 | 17 |
| 5-c | 370 | 20 | 1000 | 14 | 26 | 28 |
| 5-d | 370 | 20 | 1000 | 8 | 16 | 35 |

[1]Note that commercially available ethane typically contains impurities or other light hydrocarbons, such as methane and propane, that may reach 5 vol %. These components are considered part of the ethane component and not included in determining vol % of each component in the feed stream.

TABLE 2-1

The Catalyst Performance for Each of Cases 1 Through 5.

| | Selectivity (%) | | | | | | | | Conversion (%) | | | |
|---|---|---|---|---|---|---|---|---|---|---|---|---|
| | $C_2H_4$ | | | | $CH_3COOH$ | | | | | | | |
| Exp. | 0 | 2 | 5 | 10 | 0 | 2 | 5 | 10 | 0 | 2 | 5 | 10 |
| 1-a | 91.0 | 91.1 | 91.1 | 91.1 | 1.8 | −10.7 | −29.9 | −63.7 | 6.2 | 6.2 | 6.2 | 6.2 |
| 1-c | 74.5 | 77.5 | 80.5 | 83.0 | 6.6 | −15.8 | −65.4 | −209.0 | 46.7 | 37.5 | 24.7 | 11.9 |
| 1-e | 71.2 | 74.0 | 77.2 | | 3.6 | −25.6 | −103.8 | | 42.1 | 31.7 | 18.4 | |
| 2-a | 74.4 | 77.2 | 80.2 | 81.2 | 6.4 | −16.4 | −73.5 | −279.0 | 47.6 | 37.3 | 23.2 | 9.3 |
| 2-c | 74.9 | 77.6 | 80.8 | 82.2 | 6.7 | −18.5 | −78.0 | −253.9 | 38.2 | 31.8 | 20.7 | 10.0 |
| 2-e | 75.9 | 78.1 | 81.9 | 83.5 | 4.4 | −31.5 | −111.1 | −303.5 | 17.7 | 15.3 | 8.5 | 6.8 |
| 3-a | 77.5 | 78.7 | 81.2 | 83.0 | 5.3 | −27.2 | −94.6 | −324.1 | 30.3 | 26.3 | 18.5 | 8.3 |
| 3-c | 74.7 | 77.7 | 80.7 | 82.8 | 6.5 | −17.9 | −70.0 | −244.9 | 44.3 | 35.7 | 23.8 | 10.5 |
| 3-e | | | | | | | | | | | | |
| 4-a | 82.3 | 83.2 | 83.8 | 83.5 | 4.2 | −21.7 | −84.4 | −320.9 | 22.6 | 15.7 | 8.9 | 3.3 |
| 4-c | 74.5 | 77.5 | 80.5 | 83.0 | 6.6 | −15.8 | −65.4 | −209.0 | 46.7 | 37.5 | 24.7 | 11.9 |
| 4-e | 65.1 | 67.5 | 74.4 | 82.5 | 8.2 | −7.2 | −31.9 | −71.7 | 66.5 | 61.2 | 49.3 | 34.3 |
| 5-a | 77.0 | 78.5 | 81.3 | 83.9 | 6.1 | −1.4 | −60.1 | −30.4 | 49.1 | 45 | 26 | 30.2 |
| 5-b | 73.7 | 76.6 | 79.7 | 82.5 | 7.4 | −15.9 | −64.6 | −205.5 | 45.9 | 36.9 | 24.6 | 12.0 |
| 5-c | 76.7 | 78.6 | 80.7 | 84.5 | 6.0 | −5.4 | −26.4 | −53.9 | 52.4 | 46.8 | 37.7 | 27.8 |
| 5-d | 75.5 | 78.3 | 81.1 | 83.3 | 6.5 | −16.1 | −63.6 | −206.4 | 47.2 | 38 | 25.3 | 12.0 |

TABLE 2-2

The Process Conditions and Catalyst Performance for Each of Cases 1 Through 5.

| | Process Conditions | | | Catalyst Performance | | | |
|---|---|---|---|---|---|---|---|
| Exp. | Temp (° C.) | Pressure (psig) | GHSV ($h^{-1}$) | Ethane Conversion (%) | $C_2H_4$ Selectivity (%) | $CH_3COOH$ Selectivity (%) | $CO + CO_2$ Selectivity (%) |
| 1-a | 300 | 20 | 1000 | | | | |
| 1-c | 370 | 20 | 1000 | 62 | 88 | 1 | 11 |
| 1-e | 425 | 20 | 1000 | 61 | 91 | −5.1 | 14 |
| 2-a | 370 | 20 | 500 | 63 | 87 | 1.4 | 11 |
| 2-c | 370 | 20 | 2000 | 43 | 86 | 2.6 | 12 |
| 2-e | 370 | 20 | 10000 | 10 | 88 | −0.5 | 13 |
| 3-a | 370 | 2 | 1000 | 34 | 84 | 2.5 | 14 |
| 3-c | 370 | 14 | 1000 | 52 | 85 | 2.8 | 12 |
| 3-e | 370 | 100 | 1000 | | | | |
| 4-a | 370 | 20 | 1000 | 25 | 89 | −0.2 | 12 |
| 4-c | 370 | 20 | 1000 | 58 | 86 | 2.5 | 11 |
| 4-e | 370 | 20 | 1000 | 80 | 84 | 4.4 | 12 |
| 5-a | 370 | 20 | 1000 | 66 | 89 | 1.8 | 9 |
| 5-b | 370 | 20 | 1000 | 57 | 85 | 3.5 | 12 |
| 5-c | 370 | 20 | 1000 | 67 | 89 | 1.7 | 9 |
| 5-d | 370 | 20 | 1000 | 58 | 86 | 2.5 | 11 |

A fixed bed reactor unit (FBRU) apparatus was used to conduct experiments on addition of acetic acid in the feed stream for the oxidative dehydrogenation of ethane. The FBRU apparatus comprised two vertically oriented fixed bed tubular reactors in series, each reactor a SS316L tube with an outer diameter of 1" and a length of 34", wrapped in an electrical heating jacket and sealed with ceramic insulating material. Each reactor contained an identical catalyst bed consisting of one weight unit of catalyst to 2.14 units of weight of DENSTONE® 99 (mainly alpha alumina) powder. Total weight of the catalyst in each reactor was 143 g catalyst having the formula $MoV_{0.40}Nb_{0.16}Te_{0.14}O$, with relative atomic amounts of each component, relative to a relative amount of Mo of 1, shown in subscript. The rest of the reactors, below and above the catalyst bed was packed with quartz powder secured in place with glass wool to minimize risk of bed movement during the experimental runs.

The temperature of each of the reactors were monitored using corresponding 7-point thermocouples present in each reactor, 4 of which were situated within each catalyst bed. Temperature control, particularly at lower temperatures, was limited and resulted in fluctuations. Temperatures listed in the examples represents averages of the temperatures at the 8 different locations within the two catalyst beds. Both reactors were being controlled for temperature by controlling the pressure and boiling temperature of water inside water jackets surrounding each reactor.

For the experimental setup, a pressure transducer located immediately upstream of the first reactor was used to monitor the pressure at the inlet. The product stream leaving the second reactor was passed through condensing units before venting to air, which indicates that pressure at the point approximates 0 psig.

Cases 6 and 7 are experimental examples, conducted using the FBRU apparatus, to demonstrate the reduction to practice of selectivity to acetic acid in a physical setting. The process conditions and feed composition for each of cases 6 and 7 are summarized in Table 3. The feed composition only lists $O_2$, $C_2H_6$, $CO_2$, and acetic acid, with the balance covering the water required to bring the total up to 100 vol %. The results, including selectivity for ethylene and acetic acid, and for conversion of ethane (%), are summarized in Table 4, showing that, similar to modeling cases 1-5, adding acetic acid in the feed stream results in a decrease in selectivity for acetic acid.

TABLE 3

The Process Conditions and Feed Composition for Cases 6 and 7.

| | Process Conditions | | | Feed Composition (vol %) | | | |
|---|---|---|---|---|---|---|---|
| Exp. | Temp (° C.) | Pressure (psig) | GHSV ($h^{-1}$) | $O_2$ | $C_2H_6$[1] | $CO_2$ | $CH_3COOH$ |
| 6-a | 320 | 17.5 | 648 | 8 | 16 | 17 | 0 |
| 6-b | 320 | 18.5 | 648 | 8 | 16 | 17 | 2 |
| 7-a | 325 | 15.2 | 648 | 14 | 26 | 28 | 0 |
| 7-b | 325 | 19.3 | 648 | 14 | 26 | 28 | 3 |

[1]Note that commercially available ethane typically contains impurities or other light hydrocarbons, such as methane and propane, that may reach 5 vol %. These components are considered part of the ethane component and not included in determining vol % of each component in the feed stream.

TABLE 4

The Catalyst Performance for Cases 6 and 7.

| | Selectivity (%) | | |
|---|---|---|---|
| Exp. | $C_2H_4$ | $CH_3COOH$ | Conversion (%) |
| 6-a | 82 | 12 | 28 |
| 6-b | 82 | 2 | 28 |
| 7-a | 77 | 9 | 24 |
| 7-b | 87 | −7 | 32 |

For cases 8-11, a similar FBRU apparatus was used. For cases 8-11, the reactor temperature, inlet pressure, GHSV, feed ethane volume fraction, and feed oxygen volume fraction were kept constant. Each of cases 8-11 include two experiments, in which the first experiment ('a') included both steam and acetic acid in the feed, and the second experiment (b') included steam but no acetic acid in the feed. The reactor operating conditions and feed compositions in volume % for cases 8-11 are provided in Table 5. The catalyst activities for cases 8-11 are provided in Table 6. The extent of changes in catalyst activity and product distribution when acetic acid was present in the feed (a') in comparison to not being present in the feed (b') for cases 8-11 are provided in Table 7.

The following summarizes the trends observed for cases 8-11. The presence or absence of acetic acid in the feed did not appear to affect ethane conversion. The selectivity of ethylene either remained the same or increased when acetic acid was present in the feed (a) in comparison to not being present in the feed (b'). The selectivity of carbon monoxide/dioxide increased when acetic acid was present in the feed (a) in comparison to not being present in the feed (b'). The selectivity of acetic acid either decreased or was fully suppressed when acetic acid was present in the feed (a) in comparison to not being present in the feed (b').

In comparison to case 8, case 9 was conducted at an increased temperature of 359° C. A comparison of cases 8 and 9 revealed that there was a negligible change in acetic acid selectivity with increased temperature (Table 7), ethylene selectivity decreased while carbon monoxide/dioxide selectivity increased with increased temperature (Table 7), and an increase in ethane conversion with increased temperature (Table 6). In comparison to case 8, case 10 was conducted at an increased pressure. A comparison of cases 8 and 10 revealed that there was a decrease in the extent of decrease in acetic acid selectivity with increased pressure (Table 7), almost full suppression in extent of increase in ethylene selectivity with increased pressure (Table 7), an increase in extent of increase in carbon monoxide/dioxide selectivity with increased pressure (Table 7), and an increase in ethane conversion with increased pressure (Table 6).

From these experiments, it can be inferred that a portion of the acetic acid (when present in the feed) was being converted to ethylene, carbon monoxide, and/or carbon dioxide, and that the temperature, the pressure, or both can be decreased to shift the selectivity towards ethylene over carbon monoxide/dioxide. However, decreasing temperature, pressure, or both can also decrease ethane conversion. In some cases, a decrease in operating pressure can have a larger impact in shifting the selectivity towards ethylene over carbon monoxide/dioxide in comparison to a decrease in operating temperature. The use of multiple reactors (for example, in systems 200a and 200b) can allow for the ODH process to occur at various combinations of operating temperatures and pressures to meet both target ethane conversion and target ethylene selectivity.

TABLE 5

The Process Conditions and Feed Composition for Each of Cases 8 Through 11.

| | Process Conditions | | | Feed Composition (vol %) | | | |
|---|---|---|---|---|---|---|---|
| Exp. | Temp (° C.) | Pressure (psig) | GHSV ($h^{-1}$) | $CH_3COOH$ | $H_2O$ | $C_2H_6$ | $O_2$ |
| 8-a | 336 | 10 | 2524 | 1.5 | 73.5 | 15 | 10 |
| 8-b | 335 | 11 | 2512 | 0.0 | 75.0 | 15 | 10 |
| 9-a | 359 | 11 | 2514 | 1.5 | 73.5 | 15 | 10 |
| 9-b | 359 | 10 | 2513 | 0.0 | 75.0 | 15 | 10 |
| 10-a | 336 | 56 | 2517 | 1.5 | 73.5 | 15 | 10 |
| 10-b | 336 | 55 | 2508 | 0.0 | 75.0 | 15 | 10 |
| 11-a | 346 | 50 | 2510 | 1.5 | 73.5 | 15 | 10 |
| 11-b | 346 | 51 | 2522 | 0.0 | 75.0 | 15 | 10 |

TABLE 6

The Feed Composition and Catalyst Performance for Each of Cases 8 Through 11.

| | Feed Composition (vol %) | Ethane Conversion | Selectivity (%) | | | |
|---|---|---|---|---|---|---|
| Exp. | $CH_3COOH$ | (%) | $C_2H_4$ | $CO_2$ | CO | $CH_3COOH$ |
| 8-a | 1.5 | 6 | 85 | 7 | 10 | −2 |
| 8-b | 0 | 9 | 77 | 2 | 4 | 17 |
| 9-a | 1.5 | 19 | 78 | 10 | 14 | −2 |
| 9-b | 0 | 18 | 72 | 3 | 7 | 17 |
| 10-a | 1.5 | 23 | 60 | 11 | 13 | 16 |
| 10-b | 0 | 23 | 60 | 5 | 8 | 28 |
| 11-a | 1.5 | 26 | 61 | 12 | 15 | 12 |
| 11-b | 0 | 30 | 56 | 7 | 9 | 28 |

TABLE 7

A Comparison of Catalyst Performance for Each of Cases 8 Through 11.

| Exp. | Change in Ethane Conversion (%) | Change in Selectivity (%) | | | |
|---|---|---|---|---|---|
| | | $C_2H_4$ | $CO_2$ | CO | $CH_3COOH$ |
| 8-a vs. 8-b | −2.9 | 8.0 | 5.2 | 5.3 | −18.6 |
| 9-a vs. 9-b | 0.7 | 5.7 | 6.6 | 6.8 | −19.1 |
| 10-a vs. 10-b | 0.1 | 0.4 | 6.1 | 5.4 | −11.9 |
| 11-a vs. 11-b | −4.2 | 5.0 | 5.1 | 6.4 | −16.4 |

For case 12, the amounts of ethylene and ethane were varied in three experiments. The individual amounts of ethylene and ethane were varied, while the sum amount of ethylene and ethane in the feed remained constant. The amounts of the other components (water, oxygen, and carbon monoxide) were kept constant. For all experiments in case 12, the reactor inlet pressure was ambient pressure, WHSV was 1.29-1.31 h$^{-1}$, GHSV was 1318-1322 h$^{-1}$, and reactor temperature was 339-342° C. The feed composition, ethane conversion, and selectivity of products are provided in Table 8. The results of the experiments of case 12 show that increasing ethylene composition from 11 to 28 wt % led to an increase in selectivity towards carbon monoxide/dioxide and acetic acid, a decrease in selectivity towards ethylene, and no observable trend in ethane conversion.

TABLE 8

The Feed Composition and Catalyst Performance for Case 12.

| Exp. | Feed Composition (wt %) $H_2O/C_2H_6/C_2H_4/O_2/CO_2$ | Ethane Conversion (%) | Selectivity (%) | | | |
|---|---|---|---|---|---|---|
| | | | $C_2H_4$ | $CO_2$ | CO | $CH_3COOH$ |
| 12-a | 5/65/11/8/11 | 11 | 86 | 2 | 5 | 6 |
| 12-b | 5/58/17/8/11 | 9 | 83 | 3 | 6 | 7 |
| 12-c | 6/47/28/8/11 | 10 | 73 | 5 | 10 | 12 |

INDUSTRIAL APPLICABILITY

The present disclosure relates to a process for the oxidative dehydrogenation of ethane. The process is applicable for limiting the amount of acetic acid produced by including acetic acid, along with ethane and oxygen, as part of the feed for the ODH process.

The invention claimed is:

1. A process for the oxidative dehydrogenation of ethane comprising contacting a feed stream comprising ethane, oxygen, and acetic acid with an oxidative dehydrogenation catalyst under oxidative dehydrogenation conditions in an oxidative dehydrogenation reactor to produce a product stream comprising ethylene, unreacted ethane, water, and acetic acid, wherein the concentration of acetic acid in the feed stream is from 0.5 to 10 vol % of the feed stream.

2. The process according to claim 1, wherein the concentration of acetic acid in the feed stream is from 2 to 5 vol % of the feed stream.

3. The process according to claim 1, wherein the concentration of acetic acid in the feed stream is greater than 2 vol % of the feed stream.

4. The process according to claim 1, further comprising a downstream separation process wherein the product stream is separated into a liquid stream comprising water and acetic acid, and a gaseous components stream comprising ethylene and unreacted ethane, and recycling to the reactor as part of the feed stream at least a portion of the liquid stream.

5. The process according to claim 4, wherein the liquid stream is diluted with water to achieve the desired amount of acetic acid in the feed stream.

6. The process according to claim 4, wherein a split fraction of the liquid stream is adjusted to achieve the desired amount of acetic acid in the feed stream.

7. The process according to claim 1, wherein the feed stream to the reactor comprises:
  i) from 0.5 to 10 vol % acetic acid;
  ii) an oxygen to ethane molar ratio from 0.5 to 0.7; and
  iii) $H_2O$ and $CO_2$ in a molar ratio such that the feed composition is outside the flammability limits.

8. The process according to claim 1, wherein the reactor operates at a temperature from 300° C. to 425° C.

9. The process according to claim 1, wherein the reactor operates at a temperature from 315° C. to 400° C.

10. The process according to claim 1, wherein the reactor operates at a pressure from 0.5 psig to 100 psig.

11. The process according to claim 1, wherein the reactor operates at a pressure from 15 psig to 504 psig.

12. The process according to claim 1, wherein the gas hourly space velocity of the product stream is from 500 h$^{-1}$ to 30000 h$^{-1}$.

13. The process according to claim 1, wherein the gas hourly space velocity of the product stream is from 1000 h$^{-1}$ to 15000 h$^{-1}$.

14. The process according to claim 1, wherein the gas hourly space velocity of the product stream is from 500 h$^{-1}$ to 4000 h$^{-1}$.

15. The process according to claim 1, wherein the catalyst comprises one or more catalyst selected from the group consisting of:
  i) catalysts of the formula:

$$Mo_aV_bTe_cNb_dPd_eO_f$$

wherein: a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤ 0.10 and f is a number to satisfy the valence state of the catalyst;
  ii) catalysts of the formula:

$$Mo_aE_kG_lO_f$$

wherein: E is selected from the group consisting of Ba, Ca, Cr, Mn, Nb, Ta, Ti, Te, V, W and mixtures thereof; G is selected from the group consisting of Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to satisfy the valence state of the catalyst;
  iii) catalysts of the formula:

$$V_mMo_nNb_oTe_pMe_qO_f$$

wherein: Me is a metal selected from the group consisting of Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and iv) catalysts of the formula:

$$Mo_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

16. The process according to claim 4, wherein the liquid stream comprises less than 10 vol % of acetic acid.

17. The process according to claim 1, wherein the selectivity to ethylene is from 75% to 99%.

18. The process according to claim 1, wherein the selectivity to $CO_2$ is equal to or less than 10%.

19. The process according to claim 1, wherein the selectivity to CO is equal to or less than 11%.

20. The process according to claim 1, wherein the feed stream to the reactor comprises from 2 to 3 vol % of acetic acid, 29 to 57 vol % of $H_2O$, 16 to 26 vol % of $C_2H_6$, 8 to 14 vol % of $O_2$, and 17 to 28 vol % of $CO_2$.

21. The process according to claim 4, wherein a makeup stream and the gaseous components stream are contacted with a second oxidative dehydrogenation catalyst under oxidative dehydrogenation conditions in a second oxidative dehydrogenation reactor to produce a second product stream comprising ethylene, unreacted ethane, water, and acetic acid, wherein an overall concentration of acetic acid of the makeup stream and the gaseous components stream entering the second oxidative dehydrogenation reactor is from 0.5 to 10 vol %.

22. The process according to claim 21, further comprising a second downstream separation process wherein the second product stream is separated into a second liquid stream comprising water and acetic acid, and a second gaseous components stream comprising ethylene and unreacted ethane, and recycling at least a portion of the second liquid stream to the oxidative dehydrogenation reactor as part of the feed stream or to the second oxidative dehydrogenation reactor as part of the makeup stream.

* * * * *